United States Patent
Dantanarayana et al.

(10) Patent No.: US 7,129,257 B1
(45) Date of Patent: *Oct. 31, 2006

(54) PYRAZOLO[3,4-E]BENZOXAZOLES FOR THE TREATMENT OF GLAUCOMA

(75) Inventors: Anura P. Dantanarayana, Kandy (LK); Jesse A. May, Fort Worth, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/012,410

(22) Filed: Dec. 15, 2004

Related U.S. Application Data

(60) Provisional application No. 60/529,531, filed on Dec. 15, 2003.

(51) Int. Cl.
- A01N 43/82 (2006.01)
- A01N 43/72 (2006.01)
- A01N 43/56 (2006.01)

(52) U.S. Cl. ............ 514/360; 514/375; 514/403; 514/913

(58) Field of Classification Search ......... 514/403, 514/360, 375, 913; 548/359.5
See application file for complete search history.

(56) References Cited

U.S. PATENT DOCUMENTS

| | | | |
|---|---|---|---|
| 4,690,931 A | 9/1987 | Wick et al. | 514/317 |
| 5,011,846 A | 4/1991 | Gittos et al. | 514/294 |
| 5,151,444 A | 9/1992 | Ueno et al. | 514/530 |
| 5,290,781 A | 3/1994 | Espino et al. | 514/259 |
| 5,296,504 A | 3/1994 | Stjernschantz et al. | 514/530 |
| 5,422,368 A | 6/1995 | Stjernschantz et al. | 514/530 |
| 5,494,928 A | 2/1996 | Bös | 514/415 |
| 5,538,974 A | 7/1996 | Ogawa et al. | 514/253 |
| 5,561,150 A | 10/1996 | Wichmann | 514/406 |
| 5,571,833 A | 11/1996 | Kruse et al. | 514/414 |
| 5,578,612 A | 11/1996 | Macor et al. | 514/323 |
| 5,646,173 A | 7/1997 | Bös et al. | 514/411 |
| 5,652,272 A | 7/1997 | Ogawa et al. | 514/652 |
| 5,693,654 A | 12/1997 | Birch | 514/323 |
| 5,874,477 A | 2/1999 | McConnell et al. | 514/657 |
| 5,889,052 A | 3/1999 | Klimko et al. | 514/530 |
| 5,902,815 A | 5/1999 | Olney et al. | 514/400 |
| 6,107,324 A | 8/2000 | Behan et al. | 514/406 |
| 6,245,796 B1 | 6/2001 | Maeno et al. | 514/403 |
| 6,660,870 B1 | 12/2003 | Ruskinko et al. | 548/307.4 |
| 6,664,286 B1 | 12/2003 | May et al. | 514/415 |
| 6,696,476 B1 | 2/2004 | Chen et al. | 514/403 |
| 6,806,285 B1 | 10/2004 | May et al. | 514/416 |
| 6,881,749 B1 * | 4/2005 | Chen et al. | 514/403 |
| 6,884,816 B1 | 4/2005 | May et al. | 514/405 |
| 2003/0181503 A1 | 9/2003 | May et al. | 514/406 |

FOREIGN PATENT DOCUMENTS

| | | |
|---|---|---|
| EP | 0 771 563 B1 | 1/2003 |
| WO | WO 92/00338 | 1/1992 |
| WO | WO 94/03162 | 2/1994 |
| WO | WO 94/13275 | 6/1994 |
| WO | WO 97/35579 | 10/1997 |
| WO | WO98/18458 | 5/1998 |
| WO | WO 98/31354 | 7/1998 |
| WO | WO 99/59499 | 11/1999 |
| WO | WO 00/12475 | 3/2000 |
| WO | WO 00/12510 | 3/2000 |
| WO | WO 00/35922 | 6/2000 |
| WO | WO 00/44753 | 8/2000 |
| WO | WO 00/77002 | 12/2000 |
| WO | WO 00/77010 | 12/2000 |
| WO | WO 01/40183 | 6/2001 |
| WO | WO 01/70207 | 9/2001 |
| WO | WO 01/70223 | 9/2001 |
| WO | WO 01/70230 | 9/2001 |
| WO | WO 01/70701 | 9/2001 |
| WO | WO 01/70702 | 9/2001 |
| WO | WO 01/70745 | 9/2001 |
| WO | WO 02/098350 | 12/2002 |
| WO | WO 02/098400 | 12/2002 |
| WO | WO 02/098860 | 12/2002 |
| WO | WO 03/051291 | 6/2003 |
| WO | WO 03/051352 | 6/2003 |
| WO | WO 03/053436 | 7/2003 |
| WO | WO 04/019874 | 3/2004 |
| WO | WO 04/028451 | 4/2004 |
| WO | WO 04/054572 | 7/2004 |
| WO | WO 04/058725 | 7/2004 |

OTHER PUBLICATIONS

Bowen et al., "Nonlinear regression using spreadsheets," *Trends in Pharmacological Sciences*, vol. 16, pp. 413-423 (1995).

Chang et al., "Mechanism of the Ocular Hypotensive Action of Ketanserin," *J. of Ocular Pharmacology*, vol. 1(2), pp. 137-147 (1985).

Fiorella et al., "Role of 5-$HT_{2A}$ and 5-$HT_{2C}$ receptors in the stimulus effects of hallucinogenic drugs II: reassessment of LSD false positives," *Psychopharmacology*, vol. 121, pp. 357-363 (1995).

Gupta et al., "Therapeutic Potentials of 5-HT Receptor Modulators," *Indian J. of Pharmacology*, vol. 26, pp. 94-107 (1994).

Johnson et al., Binding to the Serotonin 5-$HT_2$ Receptor by the Enantiomers of $^{125}$I-DOI, *Neuropharmacology*, vol. 26(12, pp. 1803-1806 (1987).

Krootila et al., "Effect of Serotonin and Its Antagonist (Ketanserin) on Intraocular Pressure In the Rabbit," *J. of Ocular Pharmacology*, vol. 3(4), pp. 279-290 (1987).

Mallorga et al., "Characterization of Serotonin Receptors in the Iris + ciliary body of the albino rabbit," *Current Eye Research*, vol. 6(3), pp. 527-532 (1987).

Mano et al., "The Effect of Anplag (Sarpogelate HCL), New Selective 5-$HT_2$ Antagonist on Intraocular Pressure in Rabbits," *IOVS*, vol. 36(4), S719 (1995).

(Continued)

*Primary Examiner*—Shengjun Wang
*Assistant Examiner*—Yong S. Chong
(74) *Attorney, Agent, or Firm*—Patrick M. Ryan

(57) ABSTRACT

Pyrazolo[3,4-e]benzoxazoles and analogues thereof for lowering intraocular pressure and treating glaucoma are disclosed.

9 Claims, No Drawings

OTHER PUBLICATIONS

May et al., "A Novel and Selective 5-HT$_2$ Receptor Agonist with Ocular Hypotensive Activity: (S)-(+)-1-(2-Aminopropyl)-8,9-dihydropyrano[3,2-e]indole," *J. Med. Chem.*, vol. 46, pp. 4188-4195 (2003).

May et al., "Evaluation of the Ocular Hypotensive Response of Serotonin 5-HT$_{1A}$ and 5-HT$_2$ Receptor Ligands in Conscious Ocular Hypertensive Cynomolgus Monkeys," *J. of Pharmacology and Experimental Therapeutics*, vol. 306(1), pp. 301-309 (2003).

Osborne et al., "Do Beta-Adrenoceptors and Serotonin 5-HT$_1$A Receptors have Similar Functions in the control of Intraocular Pressure in the Rabbit?", *Ophthalmologica*, vol. 210, pp. 308-314 (1996).

Osborne et al., "5-Hydroxytryptamine$_{1A}$ agonists: potential use in glaucoma. Evidence from animal studies," *Eye*, vol. 14(38), pp. 454-463 (2000).

Takeda et al., "The Effect of Inplag. Novel Selective 5-HT$_2$ Antagonist on Intraocular Pressure in Glaucoma Patients," *IOVS*, Vo. 36(4), S734 (1995).

Wang et al., "Effect of 5-methylurapidil, an $\alpha_{1a}$-adrenergic antagonist and 5-hydroxytryptamine$_{1a}$ agonist, on aqueous humor dynamics in monkeys and rabbits," *Current Eye Research*, vol. 16(8), pp. 769-775 (1997).

Wang et al., "Effect of $_p$-MPPI Hydrochloride (p-MPPI) Applied before 5-methylurapidil (5-MU) on Intraocular Pressure (IOP) in Normal Monkeys," *IOVS*, vol. 39(4) (1998).

\* cited by examiner

PYRAZOLO[3,4-E]BENZOXAZOLES FOR THE TREATMENT OF GLAUCOMA

RELATED APPLICATIONS

This application claims priority form U.S. Patent Application Ser. No. 60/529,531, filed Dec. 15, 2003.

BACKGROUND OF THE INVENTION

The present invention relates to the use of pyrazolo[3,4-e]benzoxazoles and analogues thereof for lowering and controlling normal or elevated intraocular pressure (IOP) and for treating glaucoma.

The disease state referred to as glaucoma is characterized by a permanent loss of visual function due to irreversible damage to the optic nerve. The several morphologically or functionally distinct types of glaucoma are typically characterized by elevated IOP, which is considered to be causally related to the pathological course of the disease. Ocular hypertension is a condition wherein intraocular pressure is elevated but no apparent loss of visual function has occurred; such patients are considered to be at high risk for the eventual development of the visual loss associated with glaucoma. If glaucoma or ocular hypertension is detected early and treated promptly with medications that effectively reduce elevated intraocular pressure, loss of visual function or its progressive deterioration can generally be ameliorated. Drug therapies that have proven to be effective for the reduction of intraocular pressure include both agents that decrease aqueous humor production and agents that increase the outflow facility. Such therapies are in general administered by one of two possible routes, topically (direct application to the eye) or orally.

There are some individuals who do not respond well when treated with certain existing glaucoma therapies. There is, therefore, a need for other topical therapeutic agents that control IOP.

Serotonergic 5-$HT_{1A}$ agonists have been reported as being neuroprotective in animal models and many of these agents have been evaluated for the treatment of acute stroke among other indications. This class of compounds has been mentioned for the treatment of glaucoma (lowering and controlling IOP), see e.g., WO 98/18458 (DeSantis, et al.) and EP 0771563A2 (Mano, et al.). Osborne, et al. (Ophthalmologica, Vol. 210:308–314, 1996) teach that 8-hydroxydipropylaminotetralin (8-OH-DPAT) (a 5-$HT_{1A}$ agonist) reduces IOP in rabbits. Wang, et al. (Current Eye Research, Vol. 16(8):769–775, August 1997, and IVOS, Vol. 39(4), S488, March, 1998) indicate that 5-methylurapidil, an $\alpha_{1A}$ antagonist and 5-$HT_{1A}$ agonist lowers IOP in the monkey, but attribute the IOP effect to its $\alpha_{1A}$ receptor activity. Also, 5-$HT_{1A}$ antagonists are disclosed as being useful for the treatment of glaucoma (elevated IOP) (e.g., WO 92/0338, McLees). Furthermore, DeSai, et al. (WO 97/35579) and Macor, et al. (U.S. Pat. No. 5,578,612) relate to the use of 5-$HT_1$ and 5-$HT_{1-like}$ agonists for the treatment of glaucoma (elevated IOP). These anti-migraine compounds, e.g., sumatriptan and naratriptan and related compounds, are 5-$HT_{1B,D,E,F}$ agonists.

It has been found that serotonergic compounds which possess agonist activity at 5-$HT_2$ receptors effectively lower and control normal and elevated IOP and are useful for treating glaucoma, see U.S. Pat. No. 6,664,286 incorporated in its entirety by reference herein. Compounds that act as agonists at 5-$HT_2$ receptors are well known and have shown a variety of utilities, primarily for disorders or conditions associated with the central nervous system (CNS). U.S. Pat. No. 5,494,928 relates to certain 2-(indol-1-yl)-ethylamine derivatives that are 5-$HT_{2C}$ agonists for the treatment of obsessive compulsive disorder and other CNS derived personality disorders. U.S. Pat. No. 5,571,833 relates to tryptamine derivatives that are 5-$HT_2$ agonists for the treatment of portal hypertension and migraine. U.S. Pat. No. 5,874,477 relates to a method for treating malaria using 5-$HT_{2A/2C}$ agonists. U.S. Pat. No. 5,902,815 relates to the use of 5-$HT_{2A}$ agonists to prevent adverse effects of NMDA receptor hypo-function. WO 98/31354 relates to 5-$HT_{2B}$ agonists for the treatment of depression and other CNS conditions. WO 00/12475 relates to indoline derivatives, and WO 00/12510 and WO 00/44753 relate to certain indole derivatives as 5-$HT_{2B}$ and 5-$HT_{2C}$ receptor agonists for the treatment of a variety of disorders of the central nervous system, but especially for the treatment of obesity. WO 00/35922 relates to certain pyrazino[1,2-a]quinoxaline derivates as 5-$HT_{2C}$ agonists for the treatment of obsessive compulsive disorder, depression, eating disorders, and other disorders involving the CNS. WO 00/77002 and WO 00/77010 relate to certain substituted tetracyclic pyrido[4,3-b]indoles as 5-$HT_{2C}$ agonists with utility for the treatment of central nervous system disorders including obesity, anxiety, depression, sleep disorders, cephalic pain, and social phobias among others. Agonist response at the 5-$HT_{2A}$ receptor is reported to be the primary activity responsible for hallucinogenic activity, with some lesser involvement of the 5-$HT_{2C}$ receptor possible [Psychopharmacology, Vol. 121: 357, 1995].

U.S. Pat. No. 5,561,150 relate to certain tricyclic pyrazole derivative compounds which are identified as being 5-$HT_{2C}$ agonists for the treatment of CNS diseases and are primarily directed to lipophilic analogs that have a high probability of entering the brain. Similarly, U.S. Pat. No. 6,245,796 relates to tricyclic 5-$HT_{2C}$ agonists for the treatment of CNS diseases. This patent includes claims to certain substituted pyrazolo[3,4-e]benzoxazoles though no specific examples are provided. All the patents and publications mentioned above and throughout are incorporated in their entirety by reference herein.

5-Hyroxytryptamine (serotonin) does not cross the blood-brain barrier and enter the brain. However, in order to increase brain serotonin levels the administration of 5-hydroxy-tryptophan can be employed. The transport of 5-hydroxy-tryptophan into the brain readily occurs, and once in the brain 5-hydroxy-tryptophan is rapidly decarboxylated to provide serotonin.

Accordingly, there is a need to provide new compounds which avoid the disadvantages described above and which provide increased chemical stability and a desired length of therapeutic activity, for instance, in decreasing intraocular pressure and treating glaucoma.

SUMMARY OF THE PRESENT INVENTION

A feature of the present invention is to provide novel compounds which are 5-$HT_2$ agonists.

Another feature of the present invention is to provide compounds which have increased chemical stability and which are useful in lowering and controlling normal or elevated intraocular pressure and/or treating glaucoma.

Another feature of the present invention is to provide compounds which provide a desired level of therapeutic activity in lowering and controlling normal or elevated intraocular pressure and/or treating glaucoma.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

To achieve these and other advantages, and in accordance with the purposes of the present invention, as embodied and broadly described herein, the present invention relates to a compound having the Formula I:

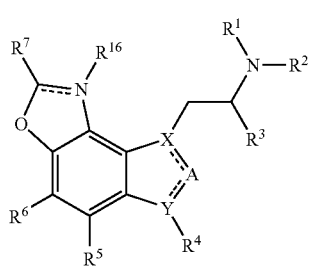

Formula I and being described more fully below.

The present invention further relates to pharmaceutical compositions containing at least one compound of Formula I.

The present invention further relates to methods to lower and/or control normal or elevated intraocular pressure by administering an effective amount of a composition containing a compound having Formula I as described above.

The present invention also relates to a method for treating glaucoma which involves administering an effective amount of a composition containing a compound having Formula I as described above.

It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to a variety of compounds which are useful according to the present invention. These compounds are represented by the following Formula I:

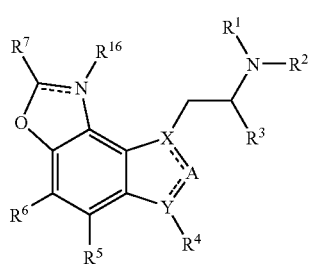

Formula I

Wherein $R^1$ and $R^2$ are independently chosen from hydrogen, $C_{1-4}$alkyl;

$R^3$ is selected from hydrogen, $C_{1-4}$alkyl, or $R^2$ and $R^3$ can complete a pyrrolidine or piperidine ring, which can be substituted with $C_{1-4}$alkyl;

$R^4$ is hydrogen, $C_{1-4}$alkyl, or when Y is carbon $R^4$ can also be halogen;

$R^5$ and $R^6$ are independently chosen from hydrogen, halogen, $C_{1-6}$alkyl, $C_{1-6}$alkylthio, $C_{1-6}$alkylsulfonyl, $C_{1-6}$alkylsulfoxide, nitrile, $C_{1-6}$alkyl substituted with halogen;

$R^7$ is chosen from C=$OR^9$, $S(O)_m R^{10}$, $NR^1$—(C=O)—$R^{11}$, $C_{1-6}$alkyl substituted with: hydroxyl, $C_{1-6}$alkoxy, $NR^{12}R^{13}$, $CO_2H$, $CO_2C_{1-6}$alkyl, $C(=O)NR^{12}R^{13}$ or $S(O)_m NR^{12}R^{13}$, or a saturated or unsaturated 5 or 6-membered heterocyclic ring which can contain 1–4 heteroatoms selected from N, O, or S and can be unsubstituted or substituted with $C_{1-4}$alkyl;

or $R^7$ can be chosen from a heterocyclic ring selected from oxazol-2-yl, 4,5-dihydro-oxazol-2-yl, 5,6-dihydro-[1,3]oxazin-2-yl, thiazol-2-yl, 4,5-dihydro-thiazol-2-yl, benzoxazol-2-yl, benzothiazol-2-yl, imidazol-2-yl, imidazolidin-2-yl, [1,2,4]oxadiazol-5-yl, [1,2,4]oxadiazol-3-yl, [1,2,4]thiadiazol-5-yl, or [1,2,4]thiadiazol-3-yl which can be unsubstituted or substituted with $C_{1-4}$alkyl;

but $R^7$ cannot be hydrogen, lower alkyl, hydroxyl, lower alkoxy, amino, mono- or di-loweralkyl amino, lower alkanoylamino, or halogen;

$R^9$ is chosen from hydroxyl, $C_{1-6}$alkoxy, $NR^{14}R^{15}$, $C_{1-6}$alkyl, or $C_{2-6}$alkyl substituted with hydroxyl, $C_{1-6}$alkoxy, $NR^{12}R^{13}$, $CO_2H$, $CO_2C_{1-6}$alkyl, $S(O)_m NR^{12}R^{13}$, halogen, or a heterocyclic ring selected from pyrrolidin-2-yl, imidazo-2-yl, imidazo-4-yl, morpholin-3-yl, oxazolyl, isoxazolyl, thiazolyl, or tetrazolyl, which can be unsubstituted or substituted with $C_{1-4}$alkyl;

$R^{10}$ is chosen from $NR^{12}R^{13}$, $C_{1-6}$alkyl, or $C_{2-6}$alkyl substituted with hydroxyl, $C_{1-6}$alkoxy, $NR^{11}R^{12}$, $CO_2H$, $CO_2C_{1-6}$alkyl;

$R^{11}$ is $C_{1-6}$alkyl substituted with hydroxyl, $C_{1-6}$alkoxy, or a saturated or unsaturated 5 or 6-membered heterocyclic ring which can contain 1–4 heteroatoms selected from N, O, or S and can be unsubstituted or substituted with $C_{1-4}$alkyl;

$R^{12}$ and $R^{13}$ are independently selected from hydrogen, $C_{1-6}$alkyl, $C_{2-6}$alkyl substituted with hydroxyl, $C_{1-6}$alkoxy, or halogen, or $R^{12}$, $R^{13}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy or $C_{1-4}$alkoxy;

$R^{14}$ and $R^{15}$ are independently selected from hydrogen, $C_{1-6}$alkyl, hydroxyl, $C_{1-6}$alkoxy, $C_{2-6}$alkyl substituted with hydroxyl, $C_{1-6}$alkoxy, halogen or a heterocyclic ring selected from pyrrolidin-2-yl, imidazo-2-yl, imidazo-4-yl, morpholin-3-yl, oxazolyl, isoxazolyl, thiazolyl, tetrazolyl, which can be unsubstituted or substituted with $C_{1-4}$alkyl, or $R^{14}$, $R^{15}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy or $C_{1-4}$alkoxy;

---=a double or single bond in the oxazole ring;

when R$^{16}$ is no atom, --- is a double bond, and when --- is a single bond, R$^7$ is Q, where Q is oxygen, sulfur, or NR$^1$ attached to the oxazole ring by a double bond;

m is 0–2;

A is N or CH;

X and Y are either N or C, wherein X and Y cannot be the same; and the dashed bonds in this ring denote a suitably appointed single and double bond;

Pharmaceutically acceptable salts and solvates, and prodrug forms of the compounds of Formula I are also part of the present invention. Certain compounds of Formula I can contain one or more chiral centers. The present invention contemplates all enantiomers, diastereomers, and mixtures thereof.

In the above definitions, the total number of carbon atoms in a substituent group is indicated by the $C_{i-j}$ prefix where the numbers i and j define the number of carbon atoms. This definition includes straight chain, branched chain, and cyclic alkyl or (cyclic alkyl)alkyl groups. A substituent may be present either singly or multiply when incorporated into the indicated structural unit. For example, the substituent halogen, which means fluorine, chlorine, bromine, or iodine, would indicate that the unit to which it is attached may be substituted with one or more halogen atoms, which may be the same or different.

Preferred are compounds of Formula I wherein:

A=N;

X=N;

Y=C; and

--- in the oxazole ring is a double bond; and pharmaceutically acceptable salts, solvates and prodrugs thereof.

Of the preferred compounds, most preferred are those compounds of Formula I wherein:

R$^1$ and R$^2$=H.

Among these compounds, especially preferred are the compounds of Formula I wherein:

R$^3$=methyl.

The term "alkanoylamino" represents a group that is linked by an amino atom that is connected to a carbon atom has a double bond to an oxygen group and a single bond to a carbon atom or hydrogen atom.

The term "acyloxy" represents a group that is linked by an oxygen atom that is connected to a carbon that has a double bond to an oxygen atom and single bond to another carbon atom.

The term "alkenyl" includes straight or branched chain hydrocarbon groups having 1 to 15 carbon atoms with at least one carbon—carbon double bond. The chain hydrogens may be substituted with other groups, such as halogen. Preferred straight or branched alkeny groups include, allyl, 1-butenyl, 1-methyl-2-propenyl and 4-pentenyl.

The term "alkoxy" represents an alkyl group attached through an oxygen linkage.

The term "alkyl" includes straight, branched or cyclic aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "alkylamino" represents an alkyl group attached through a nitrogen linkage.

The term "alkynyl" includes straight or branched chain hydrocarbon groups having 1 to 15 carbon atoms with at least one carbon—carbon triple bond. The chain hydrogens may be substituted with other groups, such as halogen. Preferred straight or branched alkynyl groups include, 2-propynyl, 2-butynyl, 3-butynyl, 1-methyl-2-propynyl and 2-pentynyl.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "carbonyl" represents a group that has a carbon atom that has a double bond to an oxygen atom.

The term "carbonylalkoxy" represents a group that is linked by a carbon atom that has a double bond to an oxygen atom and a single bond to an alkoxy group.

The term "cationic salt moiety" includes alkali and alkaline earth metal salts as well as ammonium salts.

The term "carbonyloxyl" represents a group that is linked by a carbon atom that has a double bond to an oxygen atom and a single bond to a second oxygen atom.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl or lower alkyl. Preferred cycloalkyl groups include cyclopropyl, cyclobutyl, cylopentyl and cyclohexyl.

The term "dialkylamino" represents two alkyl groups attached through a nitrogen linkage.

The term "halogen" and "halo" represents fluoro, chloro, bromo, or iodo.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "lower alkyl" represents alkyl groups containing one to six carbons ($C_1$–$C_6$).

Synthesis

Compounds of Formula I can be prepared by using one of several synthetic procedures. Pg denotes a suitable protective group to assure that a particular atom is not modified during the indicated chemical reaction.

Scheme 1

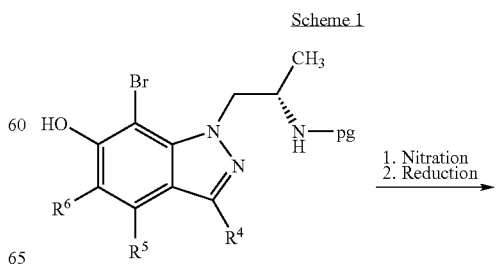

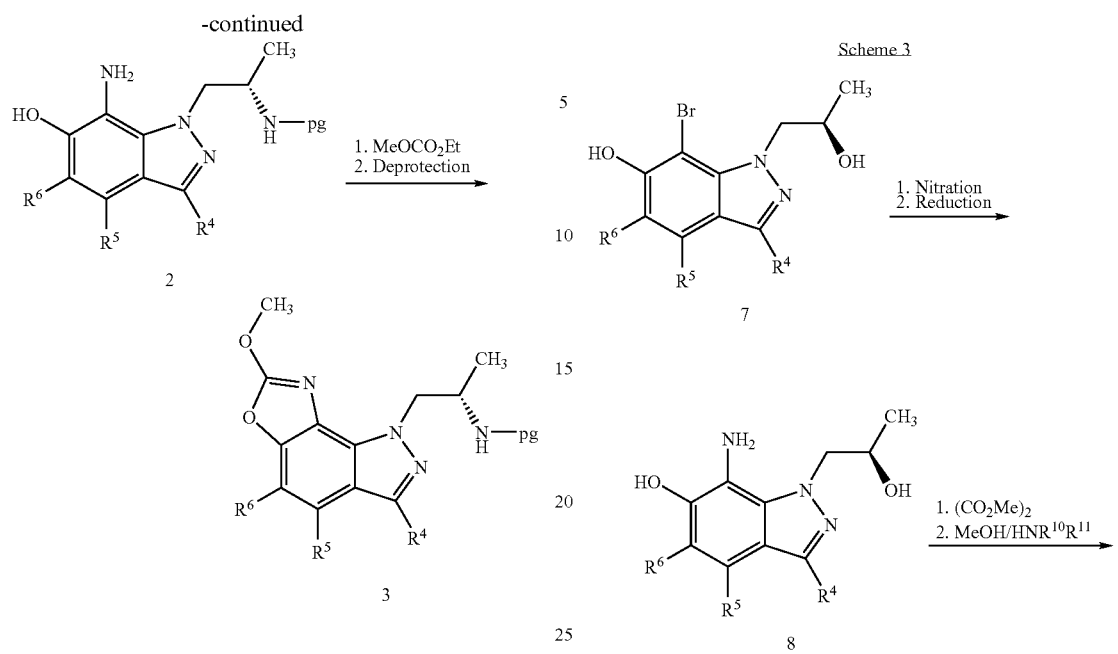
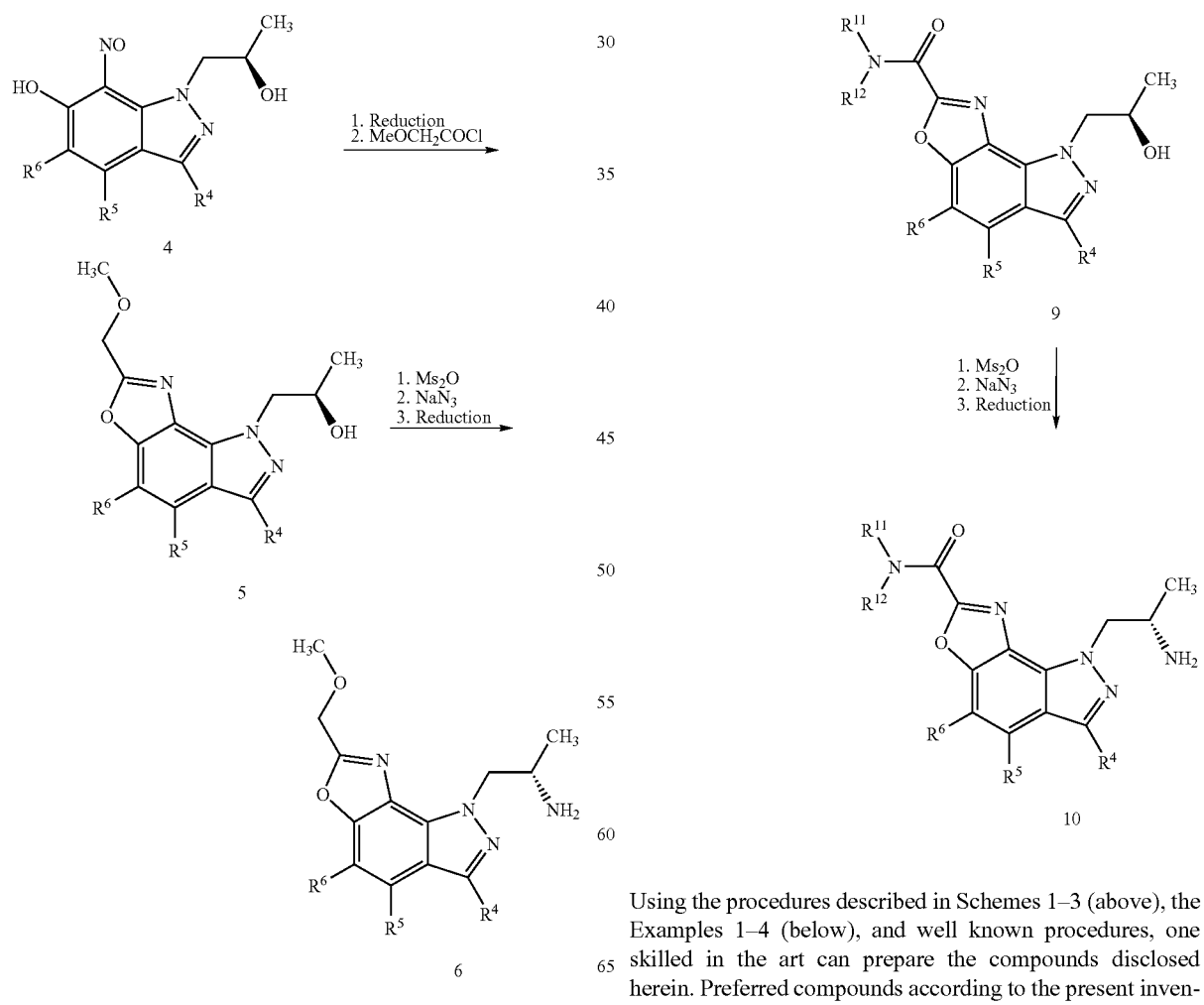
Using the procedures described in Schemes 1–3 (above), the Examples 1–4 (below), and well known procedures, one skilled in the art can prepare the compounds disclosed herein. Preferred compounds according to the present invention are those set forth in Table 1 below.

EXAMPLE 1

(S)-2-(7-Methoxy-1H-pyrazolo[3,4-e]benzoxazol-1-yl)-1-methylethylamine

Step A. [(S)-2-(6-Hydroxy-indazol-1-yl)-1-methylethyl]-carbamic acid benzyl ester 1-((S)-2-Aminopropyl)-1H-indazol-6-ol [prepared in accordance with commonly owned WO 02/098862A1, the contents of which are by this reference incorporated herein] (2.00 g, 10.5 mmol) was suspended in THF (20 mL) and saturated aqueous sodium bicarbonate (10 mL) and benzyl chloroformate (1.50 mL, 15 mol) were added. The mixture was stirred at room temperature until the starting amine dissolved. Saturated aqueous sodium bicarbonate (150 mL) was added and the reaction mixture extracted with ethyl acetate (3×150 mL). The combined organic layers were dried (magnesium sulfate), filtered, and evaporated to give a tan foam (2.65 g, 78%) which was pure by LC/MS (+APCI) m/z 326 (M+H$^+$).

Step B: Benzyl (S)-2-(7-bromo-6-hydroxy-1H-indazol-1-yl)-1-methylethylcarbamate A solution of benzyl (S)-2-(6-hydroxy-1H-indazol-1-yl)-1-methylethylcarbamate (3.00 g, 9.23 mmol) from Step A in tetrahydrofuran (30 mL) was cooled in an ice bath, small portions of N-bromosuccinimide (1.64 g, 9.23 mmol) were added and the mixture was stirred for a few minutes followed by the addition of a saturated aqueous solution of sodium sulfite (150 mL). The mixture was extracted with ethyl acetate (2×100 mL). The combined extracts were dried over magnesium sulfate, filtered, and evaporated to a white solid (3.76 g): mp 40° C.; LC/MS m/z 404/406.

Step C: Benzyl (S)-2-(6-hydroxy-7-nitro-1H-indazol-1-yl)-1-methylethylcarbamate A solution of the product from Step B (3.76 g, 9.3 mmol) in tetrahydrofuran (20 mL) and acetic acid (10 mL) was cooled in an ice bath, sodium nitrate (1.93 g, 27.9 mmol) was added and the reaction mixture was stirred for 1 h followed by warming to room temperature and stirring for one hour. Water (150 mL) was added to the reaction mixture, which was extracted with ethyl acetate (2×100 mL). The combined extracts were washed with a saturated aqueous solution of sodium bicarbonate (2×100 m), dried over magnesium sulfate, filtered, and evaporated to an oil (2.87 g). This residue was purified by chromatography (silica gel, hexane/ethyl acetate) to give a tan foam (2.44 g, 71%): LC/MS m/z 371. This was used in the next reaction without further purification.

Step D: Benzyl (S)-2-(7-amino-6-hydroxy-1H-indazol-1-yl)-1-methylethylcarbamate The product from Step C (0.20 g, 0.54 mmol) was combined with acetic acid (5 mL), water (5 mL), and iron powder (0.30 g mmol) and stirred at room temperature for 1 h. The reaction mixture was filtered and evaporated to a dark oil (0.47 g) which was was used in the next reaction: LC/MS m/z 341.

Step E: Benzyl (S)-2-(7-methoxy-1H-pyrazolo[3,4-e]benzoxazol-1-yl)-1-methylethylcarbamate The product from Step D (0.47 g) was combined with tetramethyl orthocarbonate (15 mL), p-toluenesulfonic acid hydrate (10 mg) and the mixture was stirred at room temperature for 1 h. The reaction was quenched with triethylamine (1 ml) and the reaction mixture was evaporated to a residue which was purified by chromatography (silica gel, hexane/ethyl acetate gradient) to give a colorless oil (60 mg): LC/MS m/z 381.

Step F: (S)-2-(7-Methoxy-1H-pyrazolo[3,4-e]benzoxazol-1-yl)-1-methylethylamine To a solution of the product from Step E (60 mg, 0.157 mmol) in methanol (10 mL) was added 10% palladium-on-carbon (20 mg) and the mixture was stirred under an atmosphere of hydrogen at room temperature for 18 h. The reaction mixture was filtered and evaporated to a colorless oil (30 mg): LC/MS m/z 247.

EXAMPLE 2

(S)-2-[7-(Methoxymethyl)-1H-pyrazolo[3,4-e]benzoxazol-1-yl]-1-methylethylamine

Step A: 1-[(R)-2-hydroxypropyl]-7-nitroso-1H-indazol-6-ol

To a solution of 1-[(R)-2-hydroxypropyl]-1H-indazol-6-ol (2.0 g, 1.04 mmol) in acetic acid (20 mL) was added sodium nitrite (0.72 g, 10.4 mol) and the mixture was stirred at room temperature for 1 hour. Water (200 mL) was added and the mixture was extracted with ethyl acetate (2×200 mL). The combined extracts were washed with water (200 mL), and a saturated aqueous solution of sodium bicarbonate (200 mL), dried over magnesium sulfate, filtered and evaporated to a residue which was purified by chromatography (silica gel, hexane/ethyl acetate gradient) to give a red solid (1.07 g, 47%): LC/MS m/z 222.

Step B: (R)-1-[7-(Methoxymethyl)-1H-pyrazolo[3,4-e]benzoxazol-1-yl]propan-2-ol A solution of the product from Step A (1.05 g, 4.75 mol) in tetrahydrofuran (50 mL) containing 10% palladium-on-carbon (0.1 g) was stirred under an atmosphere of hydrogen at room temperature for 18 hours. The reaction mixture was filtered, pyridine (1.0 mL, 12.3 mol) and methoxy acetyl chloride (0.43 mL, 4.75 mol) were added, and this mixture was stirred at room temperature. More pyridine (5.0 mL) was added and the reaction mixture was stirred at room temperature for 20 minutes followed by the addition of 4-dimethylaminopyridine (0.1 g); this mixture was heated at 60° C. for 3 hours followed by removal of solvents by heating at 220° C. for 30 minutes. The resulting dark liquid was purified by chromatography (silica gel, hexane/ethyl acetate gradient) to give a yellow oil (200 mg, 16%): LC/MS m/z 262.

Step C: 1-[(S)-2-Azidopropyl]-7-(methoxymethyl)-1H-pyrazolo[3,4-e]benzoxazole A solution of the product from Step B (0.20 g, 0.77 mmol in tetrahydrofuran (10 mL) was cooled (ice bath), triethylamine (0.43 mL, 3.06 mmol) and methanesulfonic anhydride (0.24 g, 1.38 mmol) were added and the mixture was stirred at 0° C. for 20 minutes. Sodium azide (0.50 g, 7.66 mmol) was added to the reaction mixture, which was evaporated to a residue that was dissolved in dimethyl sulfoxide (10 mL) and heated at 90–100° C. for 2 hours. The reaction mixture was cooled to room temperature, water (200 mL) was added, and the mixture was extracted with ethyl acetate (2×100 mL). The combined extracts were dried (magnesium sulfate), filtered, and evaporated to give a residue which was purified by chromatography (silica gel, hexane/ethyl acetate) to give a yellow oil (80 mg, 37%): LC/MS m/z 287.

Step D: (S)-2-[7-(Methoxymethyl)-1H-pyrazolo[3,4-e]benzoxazo-1-yl]-1-methylethylamine A solution of the product of Step C (80 mg, 0.28 mmol) in methanol (10 mL) containing 10% palladium-on-carbon (10 mg) was stirred under an atmosphere of hydrogen for 18 hours. The reaction mixture was filtered and evaporated to give a yellow solid (60 mg, 83%): mp 40–43° C.; LC/MS m/z 261.

EXAMPLE 3

1-[(S)-2-Aminopropyl]-1H-pyrazolo[3,4-e]benzoxazole-7-carboxylic acid amide

Step A: 7-Bromo-1-[(R)-2-hydroxypropyl]-1H-indazol-6-ol

A solution of 1-[(R)-2-hydroxypropyl]-1H-indazol-6-ol (4.76 g, 24.8 mmol) in tetrahydrofuran (50 mL), cooled in an ice bath, added small portions of N-bromosuccinimide (4.41 g, 24.8 mmol) and stirred while the reaction warmed to room temperature. The reaction was quenched with aqueous saturated sodium sulfite (100 mL) and extracted with ethyl acetate (100 mL). The combined extracts were dried (magnesium sulfate), filtered and evaporated to a yellow solid (7 g): mp 134–136° C.; LC/MS m/z 271/273.

Step B: 1-[(R)-2-Hydroxypropyl]-7-nitro-1H-indazol-6-ol

A solution of the product from Step A (6.99 g, 24.8 mmol) in a mixture of tetrahydrofuran (20 mL) and acetic acid (20 mL) was cooled in an ice bath. Sodium nitrite (5.13 g, 74.4 mol) was added and the mixture was stirred for one hour, warmed to room temperature and stirring continued for one hour. Water (200 mL) was added to the reaction mixture, which was extracted with ethyl acetate (200 mL). The organic layer was washed with aqueous saturated sodium bicarbonate (100 mL, to pH 7), dried (magnesium sulfate), filtered and saturated sodium bicarbonate (100 mL, to pH 7), dried (magnesium sulfate), filtered and evaporated to an oil (4.75 g). Purification by chromatography gave a bright yellow solid (2.96 g, 50%): mp 70–74° C.; LC/MS m/z 238.

Step C: 7-Amino-1-[(R)-2-hydroxypropyl]-1H-indazol-6-ol

To a solution of the product from Step B (1.84 g, 7.76 mmol) in methanol (20 mL) was added palladium-on-carbon (100 mg) and this mixture was stirred under a hydrogen atmosphere at room temperature for 4 h. The reaction mixture was filtered (avoiding air) and evaporated to a colorless oil: LC/MS m/z 208. This oil was immediately carried into the next step.

Step D: 1-[(R)-2-Hydroxypropyl]-1H-pyrazolo[3,4-e]benzoxazole-7-carboxylic acid amide To a solution of the product from Step C (1.61 g, 7.76 mmol) in methanol (20 mL) was added dimethyl oxalate (9.16 g, 77.6 mmol), p-toluene sulfonic anhydride hydrate (50 mg), and the mixture was heated to distill off liquids with a bath temperature of 120° C. for 5 h. The dark residue was treated with methanolic ammonia (7 M, 22 mL, 0.15 mol) and heated at reflux temperature for 1 h. Additional ammonia (7 M in methanol, 20 mL) was added and heating continued for another hour. The reaction mixture was cooled to room temperature, filtered, and evaporated to a brown solid that was purified by chromatography to give a tan solid (0.91 g, 45%): LC/MS m/z 279.

Step E: 1-[(S)-2-Azidopropyl]-1H-pyrazolo[3,4-e]benzoxazole-7-carboxylic acid amide To a suspension of the product from Step D (0.90 g, 3.45 mmol) in tetrahydrofuran (20 mL) was added triethylamine (1.93 mL, 13.9 mmol); this mixture was cooled (ice bath), methane sulfonic anhydride (1.20 g, 6.92 mmol) was added, and the mixture was stirred for 20 minutes. Sodium azide (2.25 g, 34.6 mmol) was added and the mixture was evaporated to a residue which dissolved in dimethyl sulfoxide (20 mL) and heated at 90° C. for 2.5 hours. The reaction mixture was cooled to room temperature, water (200 mL) was added, and the mixture was extracted with ethyl acetate (2×100 mL). The combined extracts were washed with water (100 mL), dried (magnesium sulfate), filtered, and evaporated to solid (0.97 g). This residue was purified by chromatography (silica gel, ethyl acetate gradient) and recrystallized from methanol and ethyl acetate to give a colorless solid (0.18 g, 18%): mp 162–164° C.; LC/MS m/z 286.

Step F: 1-[(S)-2-Aminopropyl]-1H-pyrazolo[3,4-e]benzoxazole-7-carboxylic acid amide To a solution of the product from Step E (0.18 g, 0.631 mmol) in methanol (10 mL) was added 10% palladium-on-carbon (20 mg). This mixture was maintained under an atmosphere of hydrogen at room temperature for three days. The reaction mixture was filtered and evaporated to a tan solid (0.16 g): mp 60–65° C.; LC/MS m/z 260. Analysis. Calculated for $C_{12}H_{13}N_5O_2 \cdot 0.5\ CH_3OH$: C, 54.54; H, 5.49; N, 25.44. Found: C, 54.79; H, 5.35; N, 25.29.

EXAMPLE 4

1-[(S)-2-Aminopropyl]-1H-pyrazolo[3,4-e]benzoxazole-7-carboxylic acid methylamide This compound was prepared in a manner essentially identical to that described in Example 3, but using a solution of methylamine in methanol (2 M) in Step D rather than a solution of ammonia in methanol, to give an amorphous foam (100 mg): LC/MS 274 m/z; $^1$H NMR was consistent with the assigned structure.

The compounds of the present invention can be used to lower and control IOP including IOP associated with normotension glaucoma, ocular hypertension, and glaucoma in warm blooded animals including humans and other mammals. Since the treatment of glaucoma is preferably with compounds that do not enter the CNS, relatively polar compounds that are 5-HT$_2$ agonists are of particular interest. The compounds are preferably formulated in pharmaceutical compositions which are preferably suitable for topical delivery to the eye of the patient.

The compounds of this invention, Formula I, can be incorporated into various types of pharmaceutical compositions, such as ophthalmic formulations for delivery to the eye (e.g., topically, intracamerally, or via an implant). The compounds are preferably incorporated into topical ophthalmic formulations for delivery to the eye. The compounds may be combined with ophthalmologically acceptable preservatives, viscosity enhancers, penetration enhancers, buffers, sodium chloride, and water to form an aqueous, sterile ophthalmic suspension or solution. Ophthalmic solution formulations may be prepared by dissolving a compound in a physiologically acceptable isotonic aqueous buffer. Further, the ophthalmic solution may include an ophthalmologically acceptable surfactant to assist in dissolving the compound. Furthermore, the ophthalmic solution may contain an agent to increase viscosity, such as hydroxymethylcellulose, hydroxyethylcellulose, hydroxypropylmethylcellulose, methylcellulose, polyvinylpyrrolidone, or the like, to improve the retention of the formulation in the conjunctival sac. Gelling agents can also be used, including, but not limited to, gellan and xanthan gum. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-974, or the like, according to the published formulations for analogous ophthalmic preparations; preservatives and tonicity agents can be incorporated.

The compounds are preferably formulated as topical ophthalmic suspensions or solutions, with a pH of about 5 to 8, and more preferably about 6.5 to about 7.5. The compounds will normally be contained in these formulations in an amount 0.01% to 5% by weight, but preferably in an amount of 0.025% to 2% by weight. Thus, for topical presentation 1 to 2 drops of these formulations would be delivered to the surface of the eye 1 to 4 times per day according to the discretion of a skilled clinician.

The compounds can also be used in combination with other agents for treating glaucoma, such as, but not limited to, β-blockers (e.g., timolol, betaxolol, levobetaxolol, carteolol, levobunolol, propranolol), carbonic anhydrase inhibitors (e.g., brinzolamide and dorzolamide), α$_1$ antagonists (e.g., nipradolol), α$_2$ agonists (e.g. iopidine and brimonidine), miotics (e.g., pilocarpine and epinephrine), prostaglandin analogs (e.g., latanoprost, travoprost, unoprostone, and compounds set forth in U.S. Pat. Nos. 5,889,052; 5,296,504; 5,422,368; and 5,151,444, "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, and appropriate compounds from WO 94/13275, including memantine.

The compounds of the present invention preferably function as 5-HT$_2$ agonists and preferably do not enter the CNS. Compounds having the ability to be a 5-HT$_2$ agonist are beneficial for controlling IOP as well as the treatment of glaucoma as shown in U.S. Pat. No. 6,664,286 incorporated in its entirety by reference herein.

The compounds of the present invention preferably provide increased chemical stability and preferably achieve the desired level of therapeutic activity which includes a lowering or controlling of IOP.

The compounds of the present invention can be used in controlling or lowering IOP in warm blooded animals including humans. Preferably, an effective amount of the compound is administered to the patient such that the IOP is controlled or lowered to acceptable levels. Furthermore, the compounds of the present invention can be used to treat glaucoma in warm blooded animals, including humans, by administering an effective amount of the compound to a patient in need of such treatment to treat the glaucoma. Pharmaceutically acceptable amounts of the compounds of the present invention will be readily understood by those skilled in the art to mean amounts sufficient to effect the desired therapy without toxicity or other deleterious effects on the patients' health. Examples of such amounts include without limitation those amounts shown in the Examples.

Another embodiment of the present invention is a method of activating or binding serotonin receptors, comprising administering an effective amount of at least one compound of the present invention to a patient using an amount effective to activate or bind serotonin receptors, such as, but not limited to, the dosage levels described herein.

The procedures described herein in Method 1 can be used to confirm a compound's 5-HT$_2$ binding affinity.

Method 1

5-HT$_2$ Receptor Binding Assay

To determine the affinities of serotonergic compounds at the 5-HT$_2$ receptors, their ability to compete for the binding of the agonist radioligand [$^{125}$I]DOI to brain 5-HT$_2$ receptors is determined as described below with minor modification of the literature procedure [Neuropharmacology, 26, 1803 (1987)]. Aliquots of post mortem rat or human cerebral cortex homogenates (400 μL) dispersed in 50 mM TrisHCl buffer (pH 7.4) are incubated with [$^{125}$I]DOI (80 pM final) in the absence or presence of methiothepin (10 μM final) to define total and non-specific binding, respectively, in a total volume of 0.5 mL. The assay mixture is incubated for 1 hour at 23° C. in polypropylene tubes and the assays terminated by rapid vacuum filtration over Whatman GF/B glass fiber filters previously soaked in 0.3% polyethyleneimine using ice-cold buffer. Test compounds (at different concentrations) are substituted for methiothepin. Filter-bound radioactivity is determined by scintillation spectrometry on a beta counter. The data are analyzed using a non-linear, iterative curve-fitting computer program [Trends Pharmacol. Sci., 16, 413 (1995)] to determine the compound affinity parameter.

The concentration of the compound needed to inhibit the [$^{125}$I]DOI binding by 50% of the maximum is termed the $IC_{50}$ or $K_i$ value.

Method 2

5-HT$_2$ Functional Assay: [Ca$^{2+}$]$_i$ Mobilization

The receptor-mediated mobilization on intracellular calcium ([Ca$^{2+}$]$_i$) was studied using the Fluorescence Imaging Plate Reader (FLIPR) instrument. Rat vascular smooth muscle cells, A7r5, were grown in a normal media of DMEM/10% FBS and 10 μg/mL gentamycin. Confluent cell monolayers were trypsinized, pelleted, and re-suspended in normal media. Cells were seeded in a 50 μL volume at a density of 20,000 cells/well in a black wall, 96-well tissue culture plate and grown for 2 days.

On the day of the experiment, one vial of FLIPR Calcium Assay Kit dye was re-suspended in 50 mL of a FLIPR buffer consisting of Hank's Balanced Salt Solution (HBSS), 20 mM HEPES, and 2.5 mM probenecid, pH 7.4. Cells were loaded with the calcium-sensitive dye by addition of an equal volume (50 μL) to each well of the 96-well plate and incubated with dye for 1 h at 23° C.

Typically, test compounds were stored at 25 μM in 50% DMSO/50% Ethanol solvent. Compounds were diluted 1:50 in 20% DMSO/20% Ethanol. For "hit" screening, compounds were further diluted 1:10 in FLIPR buffer and tested at a final concentration of 10 μM. For dose-response experiments, compounds were diluted 1:50 in FLIPR buffer and serially diluted 1:10 to give a 5- or 8-point dose-response curve.

The compound plate and cell plate were placed in the FLIPR instrument. At the beginning of an experimental run, a signal test was performed to check the basal fluorescence signal from the dye-loaded cells and the uniformity of the signal across the plate. The basal fluorescence was adjusted between 8000–12000 counts by modifying the exposure time, the camera F-stop, or the laser power. Instrument settings for a typical assay were the following: laser power 0.3–0.6 W, camera F-stop F/2, and exposure time 0.4 sec. An aliquot (25 μL) of the test compound was added to the existing 100 μL dye-loaded cells at a dispensing speed of 50 μL/sec. Fluorescence data were collected in real-time at 1.0 sec intervals for the first 60 secs and at 6.0 sec intervals for an additional 120 secs. Responses were measured as peak fluorescence intensity minus basal and where appropriate were expressed as a percentage of a maximum 5-HT-induced response. When the compounds were tested as antagonists against 10 μM 5-HT, they were incubated with the cells for 15 minutes prior to the addition of 5-HT.

The above procedures were used to generate the data shown in Table 1.

TABLE 1

5-HT$_{2A}$ Receptor Binding and Functional Data

| Example | 5-HT$_{2A}$ | | |
|---|---|---|---|
| | $IC_{50}$ (nM) | $EC_{50}$ (nM) | $E_{max}$ (%) |
| 1 | 8 | 352 | 72 |
| 2 | 6 | 174 | 88 |
| 3 | | 445 | 72 |
| 4 | 19 | 907 | 77 |

The following topical ophthalmic formulations are useful according to the present invention administered 1–4 times per day according to the discretion of a skilled clinician.

EXAMPLE 5

| Ingredients | Amount (wt %) |
|---|---|
| Compound of any of Examples 1–4 | 0.01–2% |
| Hydroxypropyl methylcellulose | 0.5% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 6

| Ingredients | Amount (wt %) |
|---|---|
| Compound of any of Examples 1–4 | 0.01–2% |
| Methyl cellulose | 4.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 7

| Ingredients | Amount (wt %) |
|---|---|
| Compound of any of Examples 1–4 | 0.01–2% |
| Guar gum | 0.4–6.0% |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |
| Purified water | q.s. to 100% |

EXAMPLE 8

| Ingredients | Amount (wt %) |
|---|---|
| Compound of any of Examples 1–4 | 0.01–2% |
| White petrolatum and mineral oil and lanolin | Ointment consistency |
| Dibasic sodium phosphate (anhydrous) | 0.2% |
| Sodium chloride | 0.5% |
| Disodium EDTA (Edetate disodium) | 0.01% |
| Polysorbate 80 | 0.05% |
| Benzalkonium chloride | 0.01% |
| Sodium hydroxide/Hydrochloric acid | For adjusting pH to 7.3–7.4 |

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A method of lowering and/or controlling intraocular pressure in an eye of a patient in need thereof, comprising administering to the patient a pharmaceutically effective amount of a compound of formula I:

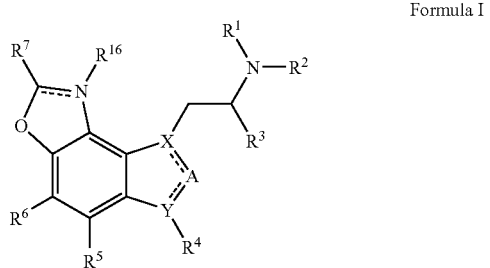

Formula I

Wherein $R^1$ and $R^2$ are independently chosen from hydrogen, $C_{1-4}$alkyl;

$R^3$ is selected from hydrogen, $C_{1-4}$alkyl, or $R^2$ and $R^3$ can complete a pyrrolidine or piperidine ring, which can be substituted with $C_{1-4}$alkyl;

$R^4$ is hydrogen, $C_{1-4}$alkyl, or when Y is carbon $R^4$ can also be halogen;

$R^5$ and $R^6$ are independently chosen from hydrogen, halogen, $C_{1-6}$alkyl, $C_{1-6}$alkylthio, $C_{1-6}$alkylsulfonyl, $C_{1-6}$alkylsulfoxide, nitrile, $C_{1-6}$alkyl substituted with halogen;

$R^7$ is chosen from $C=OR^9$, $S(O)_mR^{10}$, $NR^1—(C=O)—R^{11}$, $C_{1-6}$alkyl substituted with: hydroxyl, $C_{1-6}$alkoxy, $NR^{12}R^{13}$, $CO_2H$, $CO_2C_{1-6}$alkyl, $C(=O)NR^{12}R^{13}$ or $S(O)_mNR^{12}R^{13}$, or a saturated or unsaturated 5 or 6-membered heterocyclic ring which can contain 1–4 heteroatoms selected from N, O, or S and can be unsubstituted or substituted with $C_{1-4}$alkyl;

or $R^7$ can be chosen from a heterocyclic ring selected from oxazol-2-yl, 4,5-dihydro-oxazol-2-yl, 5,6-dihydro-[1,3]oxazin-2-yl, thiazol-2-yl, 4,5-dihydro-thiazol-2-yl, benzoxazol-2-yl, benzothiazol-2-yl, imidazol-2-yl, imidazolidin-2-yl, [1,2,4]oxadiazol-5-yl, [1,2,4]oxadiazol-3-yl, [1,2,4]thiadiazol-5-yl, or [1,2,4]thiadiazol-3-yl which can be unsubstituted or substituted with $C_{1-4}$alkyl;

but $R^7$ cannot be hydrogen, lower alkyl, hydroxyl, lower alkoxy, amino, mono- or di-loweralkyl amino, lower alkanoylamino, or halogen;

$R^9$ is chosen from hydroxyl, $C_{1-6}$alkoxy, $NR^{14}R^{15}$, $C_{1-6}$alkyl, or $C_{2-6}$alkyl substituted with hydroxyl, $C_{1-6}$alkoxy, $NR^{12}R^{13}$, $CO_2H$, $CO_2C_{1-6}$alkyl, $S(O)_m NR^{12}R^{13}$, halogen, or a heterocyclic ring selected from pyrrolidin-2-yl, imidazo-2-yl, imidazo-4-yl, morpholin-3-yl, oxazolyl, isoxazolyl, thiazolyl, or tetrazolyl, which can be unsubstituted or substituted with $C_{1-4}$alkyl;

$R^{10}$ is chosen from $NR^{12}R^{13}$, $C_{1-6}$alkyl, or $C_{2-6}$alkyl substituted with hydroxyl, $C_{1-6}$alkoxy, $NR^{11}R^{12}$, $CO_2H$, $CO_2C_{1-6}$alkyl;

$R^{11}$ is $C_{1-6}$alkyl substituted with hydroxyl, $C_{1-6}$alkoxy, or a saturated or unsaturated 5 or 6-membered heterocyclic ring which can contain 1–4 heteroatoms selected from N, O, or S and can be unsubstituted or substituted with $C_{1-4}$alkyl;

$R^{12}$ and $R^{13}$ are independently selected from hydrogen, $C_{1-6}$alkyl, $C_{2-6}$alkyl substituted with hydroxyl, $C_{1-6}$alkoxy, or halogen, or $R^{12}$, $R^{13}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy or $C_{1-4}$alkoxy;

$R^{14}$ and $R^{15}$ are independently selected from hydrogen, $C_{1-6}$alkyl, hydroxyl, $C_{1-6}$alkoxy, $C_{2-6}$alkyl substituted with hydroxyl, $C_{1-6}$alkoxy, halogen or a heterocyclic ring selected from pyrrolidin-2-yl, imidazo-2-yl, imidazo-4-yl, morpholin-3-yl, oxazolyl, isoxazolyl, thiazolyl, tetrazolyl, which can be unsubstituted or substituted with $C_{1-4}$alkyl, or $R^{14}$, $R^{15}$, and the intervening nitrogen atom can form a heterocyclic ring selected from morpholine, thiomorpholine, thiomorpholine 1-oxide, thiomorpholine 1,1-dioxide, azetidine, pyrrolidine, piperidine, piperazine, unsubstituted or substituted with $C_{1-4}$alkyl or $C_{1-4}$alkyl substituted with hydroxy or $C_{1-4}$alkoxy;

$R^{16}$ is chosen from no atom, hydrogen, $C_{1-4}$alkyl, or $C_{1-6}$alkyl substituted with halogen, HO, or $C_{1-6}$alkoxy;

--- =double or single bond in the oxazole ring; when $R^{16}$ is no atom, --- is a double bond, and when --- is a single bond, $R^7$ is Q, where Q is oxygen, sulfur, or $NR^1$ attached to the oxazole ring by a double bond;

m is 0–2;

A is N or CH;

X and Y are either N or C, wherein X and Y cannot be the same; and the dashed bonds in this ring denote a suitably appointed single and double bond; and pharmaceutically acceptable salts, solvates, or prodrugs thereof.

2. The method of claim 1, wherein the compound is administered topically.

3. The method of claim 1, wherein the compound is administered as a solution, suspension or emulsion in an ophthalmically acceptable vehicle.

4. The method of claim 1, wherein the concentration of the compound is from about 0.01 to about 2 percent by weight.

5. The method of claim 2, wherein for the compound of Formula I:

A=N;

X=N;

Y=C; and

--- in the oxazole ring is a double bond; and pharmaceutically acceptable salts, solvates and prodrugs thereof.

6. The method of claim 5, wherein for the compound of Formula I: $R^1$, $R^2$=H.

7. The method of claim 6, wherein for the compound of Formula I: $R^3$=methyl.

8. The method of claim 5, wherein the compound is administered as a solution, suspension or emulsion in an ophthalmically acceptable vehicle.

9. The method of claim 8, wherein the compound is administered as a solutin having a pH from about 6.5 to about 7.5.

* * * * *